United States Patent [19]

John

[11] Patent Number: 5,287,859

[45] Date of Patent: Feb. 22, 1994

[54] ELECTROENCEPHALOGRAPH INSTRUMENT FOR MASS SCREENING

[75] Inventor: Erwin R. John, Mamaroneck, N.Y.

[73] Assignee: New York University, New York, N.Y.

[21] Appl. No.: 951,656

[22] Filed: Sep. 25, 1992

[51] Int. Cl.$^5$ .............................................. A61B 5/04
[52] U.S. Cl. .................................................. 128/731
[58] Field of Search ................ 128/670, 731, 745, 905

[56] References Cited

U.S. PATENT DOCUMENTS

| | | | |
|---|---|---|---|
| 4,171,696 | 10/1979 | John | 128/731 |
| 4,201,224 | 5/1980 | John | 128/731 |
| 4,705,049 | 11/1987 | John | 128/731 |
| 4,862,359 | 8/1989 | Trivedi et al. | 128/731 |
| 4,913,160 | 4/1990 | John | 128/731 |
| 4,926,969 | 5/1990 | Wright et al. | 128/731 |

Primary Examiner—Max Hindenburg
Attorney, Agent, or Firm—Eliot S. Gerber

[57] ABSTRACT

In an electroencephalographic (EEG) system the number of EEG electrodes is greater than the number of amplification channels. A switching system switches the EEG electrodes to the amplification channels to provide a sequence of segments of data from each EEG electrode. The segments are compared to each other and with normal data to provide statistically reliable information regarding the normality of the patient's brain waves. In one embodiment, both EEG and EKG electrodes are alternatively connected to EKG amplifiers.

48 Claims, 2 Drawing Sheets

ELECTROENCEPHALOGRAPH INSTRUMENT FOR MASS SCREENING

BACKGROUND OF THE INVENTION

1. Field of the Invention

The present invention relates to medical instruments and more particularly to an EEG (electroencephalograph) instrument having a microprocessor based digital analysis system for screening a large population (mass) for brain disorders.

2. Related Art

At the present time a limited number of specialists in human brain disorders, such as neurologists and psychiatrists, have an EEG (electroencephalograph) in their office. Such office EEG machines typically are 2 to 8 channel instruments having 2 to 8 electrode leads which are placed on the scalp, a preamplifier and amplifier for each channel, and an analog display device such as a CRT monitor, a multi-pen strip recorder or printer. The display is of a wavy line for each channel, showing the patient's brain waves as detected at each electrode.

In addition, more complex and expensive EEG instruments are available and are generally located in hospitals or specialized neurological clinics. These instruments may use more channels, for example, from 19 to 25 channels. They may convert the analog brain wave signals into digital data, analyze the digital data using a data base of normal and abnormal patients, and may produce a topographical map showing the brain and distinguishing normal/abnormal regions by color. Increasing evidence attests to the utility of computerized quantitative analysis of the EEG (QEEG) for early detection and diagnosis of subtle brain dysfunctions. An example of such instruments is the "Spectrum 32" (Cadwell Laboratories) and see U.S. Pat. No. 4,279,258, incorporated by reference herein.

The use of EKG (electrocardiogram) instruments by physicians is much more widespread. An internist, family practitioner or general physician will usually have an EKG instrument in his/her office. Such instruments generally have 3 to 12 channels and consist of a set of electrodes, attachable at the patient's skin near the heart using a conductive gel, an amplifier for each channel, and an analog display device such as a multi-pen recorder.

It is conventional in a physical examination, for example, an annual medical check-up, for the physician to test the patient's heart using the office EKG instrument. However, routine EEG examinations are not given because most physicians do not have an EEG instrument or the training to interpret an EEG analog recording. Even in those instances where EEG screening would be particularly useful, for example, to test school-age children for attention deficit disorder or an elderly person for cerebral ischemia, such mass screening examination is not carried out due to cost, the lack of suitable EEG instruments, the lack of personnel trained to interpret the analog recordings, and the necessity for computer-assisted quantitative analysis as an adjunct to proper interpretation.

SUMMARY OF THE INVENTION

In accordance with the present invention there is provided an instrument and method which may be used by family, general and other physicians, in their offices, to examine patients during a general medical examination. The testing is rapid, less than 5 or 10 minutes, and most of the preparation and testing may be performed by a nurse or other medical assistant.

In one embodiment, the instrument uses the conventional multi-channel EKG device and adds to it, at its input, a set of input electrodes and preamplifiers. A computer system is added at the EKG output. The electrodes are removable scalp EEG electrodes. Brain waves are at the microvolt level, compared to EKG electrical activity which is at the millivolt level, so a preamplifier is connected, in each channel, between a scalp EEG electrode and an EKG amplifier. The EKG amplifiers are used without modification. If desired, the pen recorder of the EKG device can display the EEG waves being recorded to confirm that data are valid and the electrodes can be displayed sequentially. The outputs of the EKG device are connected to a special purpose computer system, which includes an A/D multiplexer and a programmed microprocessor. The computer system controls testing devices, such as a stimulator producing flashes, clicks or auditory shocks; tests the impedance of the leads to insure that their contacts with the patient are satisfactory; tests the amplification of each channel with calibration pulses; converts the amplified analog brain waves into digital data; removes artifactual contamination by electrical potentials not arising from brain activity from every recording channel; and performs an analysis of the brain waves to derive a conclusion as to "normal" or "abnormal" which is displayed to the physician.

A pair of electrodes are connected to detect eye movement, for example, on the inner and outer canthus, and the data from those electrodes is cross-correlated with data from the scalp electrodes by the computer system to provide artifact-free brain wave data by regression techniques. Periods of acceptable (artifact-free) data are joined together to form a recording session, for example, 4-6 minutes, which is recorded on a disk of the computer system. This session is divided into alternative even and odd numbered segments, each composed of 2.5 second long samples of artifact-free EEG. These even and odd samples are combined into two "split-half" samples. The computer system determines if the data obtained under each testing condition and at each tested brain wave frequency and function is acceptable by comparing these "split-half" samples of data from each electrode lead. Features extracted from the two accepted samples are compared, by the computer system, with those from a normal group, based on the patient's age. The statistics for such comparisons are stored in the computer system. The computer system, based on these comparisons, provides a "normal" or "abnormal" determination for every individual feature in both samples. Each individual determination is thresholded at the 0.05 probability level (1.96 standard deviations from the norm). In order for an "abnormal" finding to be confirmed by the proposed system, the same individual variable must be deviant from normal at the 0.05 level in both split-half samples. The probability that this could occur by chance is $P_1 \times P_2$, or $0.05 \times 0.05$, or 0.0025. This minimizes the chance of false positive findings.

In one embodiment, if the determination is "abnormal", the contents of the patient's disk is transmitted by modem, or the disk itself is sent, to a neurological analysis center where its contents are further analyzed.

In another embodiment, the system is made as a complete brain wave analysis system, without EKG amplifiers.

DETAILED DESCRIPTION OF THE INVENTION

Figure 1:
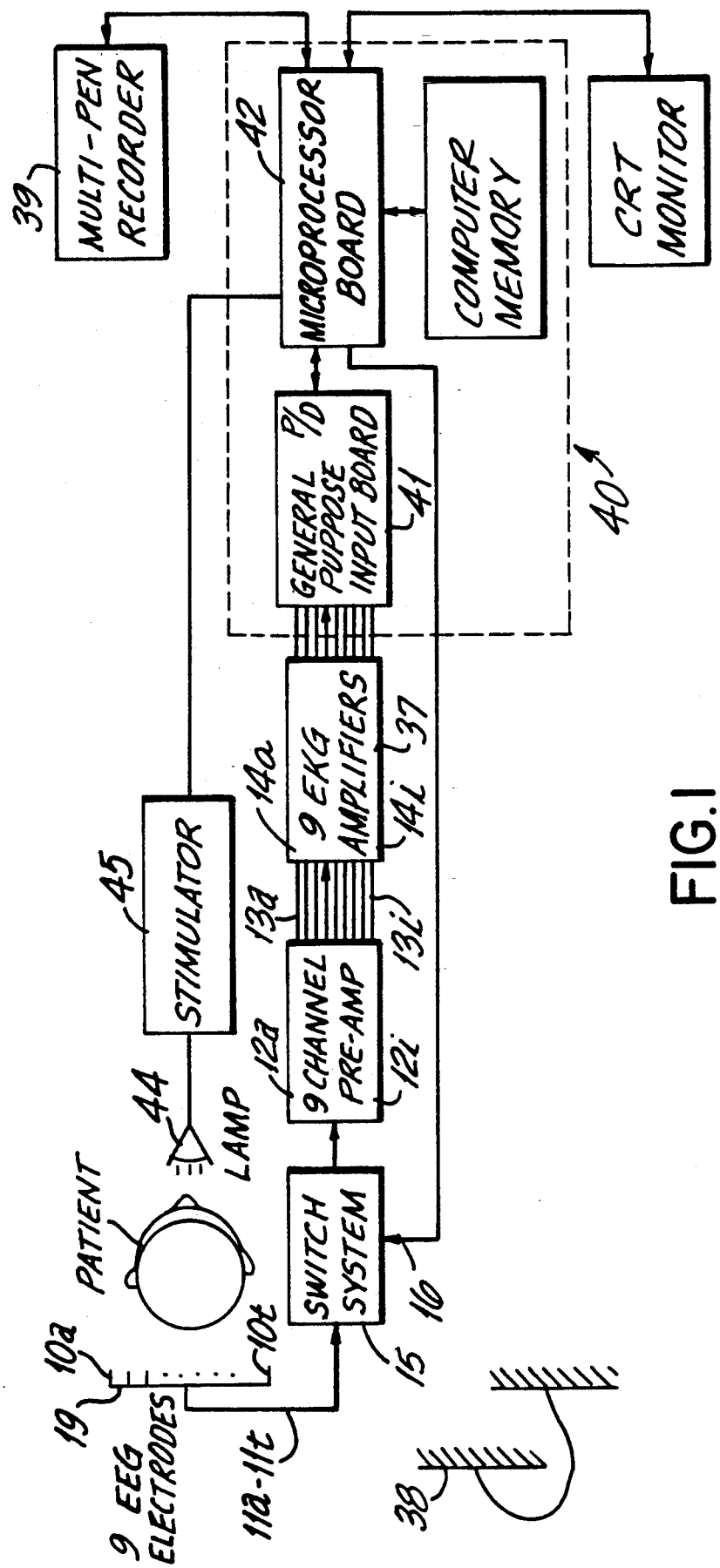
FIG. 1 is a block electronic schematic drawing of the system of the present invention.

A general block diagram of one embodiment of the present invention is shown in FIG. 1. As shown therein, a set of nineteen removable electrodes $10a-10t$ in the conventional 10/20 electrode system is attached to the scalp of the patient, or other person being examined ("patient"). Preferably the electrodes are in a stretch band or helmet. The number of electrodes is generally greater than the number of amplification channels. Generally 19 electrodes are used and as few as three amplification channels may be used. The "patients" may be, in a school screening program, all of the children of a certain age in the school population, or only those children deemed to be "at risk" because of poor school performance, frequent absences, behavior problems, etc. The "patients" might be mature adults, at risk for the degenerative diseases of aging or vulnerable to the stresses of daily life, visiting their family physician for a routine physical examination.

The patient can be stimulated by the stimulator 45. The stimulator is under control of the microprocessor 42. Generally the stimulator will be a lamp 44 which is flashed to provide a stimulus to the patient. However, alternatively, or in addition, other stimulus devices, such as video screens, loudspeakers, earphones and skin low level shock devices may be used.

The electrodes are part of an "Input-EKG" device which consists of a box 19 having the electrodes. $10a-10t$, leads $11a-11t$ to the electrodes, preamplifiers $12a-12i$ hose inputs are connected to the switch system 15 and output leads $13a-13i$, respectively, which are adapted to be plugged into the respective amplifiers $14a-14i$ of a conventional 9-channel EKG device 37. The analogous procedure can be used with any EKG instrument having at least three channels, 1 for artifact and two for the recording of EEG from symmetrical (homologous) electrodes. The EKG device 37 also has conventional EKG leads and electrodes 38 which are not used during EEG testing. In addition, the conventional EKG device has a display device, generally a multi-pen paper (hard copy) recorder 39.

The switch system 15 is controlled over line 16 by microprocessor board 42. It switches the 19 electrodes $10a-10t$ to the preamplifiers 12. For example, if only 3 preamplifiers are available, then one channel is used for a fixed or fiducial (vertex lead) and the other two channels are automatically switched, by the microprocessor board 42, between selected electrodes in a bilateral symmetric manner, i.e., 9 combinations of 2 electrodes. The fiducial lead is examined to confirm "stationerity" of state between the odd and even samples.

In the case of eight amplification channels, one is used for an EOG eye movement lead, one for EKG heartbeat, one for a fixed vertex lead, and 4 for bilateral symmetric switching (4 sets of 4 electrodes and 2 combinations of 2 electrodes or, alternatively, 5 leads used in a clockwise rotation).

Each of the preamplifiers $12a-12i$ has an input isolation means to protect against current leakage, for example, a suitable isolation means is a photo-diode light-emitting diode (LED) isolation coupler. In addition, each preamplifier input is protected from electrical interference by a radio-frequency filter and a 60-cycle notch filter. Preferably each preamplifier has a frequency range of 0.5 to 100 Hz., gain of a 10,000, common mode rejection of 160 DB, and noise of less than 1 microvolt. Such high-gain low-noise preamplifiers are presently commercially available. In addition, an inactive electrode, such as an electrode connected to the earlobe, is used to provide a common reference.

There are 3-12 amplifiers, depending on the system the physician owns, but an 9-channel (9 amplifier) device is relatively common and is here used for illustration.

The output connections of the EKG 37 would normally be connected to the multi-pen recorder 39. However, in the present invention, an output computer system 40, preferably in the same cabinet as the preamplifiers, is connected to the EKG amplifier output connections. The computer system 40 consists of a GPIB (General Purpose Input Board) 41 and a microprocessor board 42. The GPIB includes an analog-digital converter (A/D) and multiplexer 43.

An analog-to-digital multiplexer (A/D multiplexer) 43 provides a digital output from the nine analog amplifiers. The A/D multiplexer 43 samples the EEG waves (outputs of amplifiers) at a rate compatible with their bandwidths, preferably in the range of 200 to 300 times per second to comply with their 0.05 to 100 H, bandwidth.

The information from the multiplexer 43 is provided to a microprocessor 42. The microprocessor has been programmed by an external software program means, such as a floppy disk recorder, or other input system. The programmed micro-processor ("firmware") is programmed to perform the patient testing and the data analysis described below. The microprocessor may be the INTEL 386 (TM) or other comparable device.

The program and its controlled microprocessor condition the input signals and insure that they are valid biological signals. Such validity checks on the input signals include calibration testing and impedance measurements.

The computer system 40 automatically provides a timed set of stimuli of various modalities from the stimulator. The patient's brain waves will respond to each stimulus providing an "Evoked Potentialer (EP) Those brain waves are averaged to reduce noise, providing an "Average Evoked Response" (AER).

The AER is the sum of samples time locked to the onset of the stimuli divided by the number of samples, to provide an updated average. The AERs are obtained in computer 40.

Thus, the device described herein is capable of evaluating both the spontaneous electrical activity of the resting brain (EEG) and the processing of sensory information after simulation (E.P.'s).

ARTIFACT REJECTION

EEG recordings are often contaminated by potentials generated by other sources than the brain, for example, body movements. A high proportion of these artifacts produce potentials longer than the EEG voltage. A voltage threshold can be computed continuously for every EEG channel separately by calculating the r m s voltage and multiplying it by an appropriate constant (r m s voltage is approximately 0.2 standard deviations of amplitude). Segments containing voltages larger than this updated threshold are automatically rejected. Preferably the intervals (recording periods on each EEG channel) are rejected in which the voltage (signal) exceeds a multiple of the r m s voltage equal to 6 times (6×) the standard deviation of means amplitude.

EEG RECORDING WITH EEG ARTIFACT REMOVED

A major problem in the testing of patients, to obtain satisfactory EEG data, is removal of eye movement (EOG) (Electro-Oculogram) artifact. The voluntary or involuntary movement of the patient's muscles, for example, blinking of the eyes (EOG), respiration, heartbeats or head and neck muscles (EMG) may produce electrical signals which can be mistaken for EEG data. Slow eye movements, in particular, can produce artifacts difficult to exclude by simple voltage thresholds as described above. The present invention seeks to reduce the adverse effects of such EEG artifacts by a process called "removal by regression".

Two electrode channels (electrodes, preamplifiers and amplifiers) are used to detect salient artifacts. Preferably one pair of electrodes is placed oblique across an eye of the patient, to detect artifacts which arise mainly from blinking or eye movements (EOG) and another electrode is placed near the heart, to detect heartbeats (EKG).

For purpose of illustration, assume that the artifact detection channel has an EOG lead connected near the eye ("EOG") and the artifact contaminated scalp electrode signal, at one electrode, is called $EEG_i$.

Then the "regression removal" equations are:

$$EOG \times EEG_i = R_i \quad (1)$$

$$EEG_i R_i EOG = EOG_i \text{ (uncontaminated)} \quad (2)$$

Equation (1) above is the correlation between each one of the EEG channel, signals ($EEG_1$) and the EOG channel signal. Equation (2) is the regression removal of the EOG signal from the $EEG_1$ channel signal.

The eye movement artifact is lessened by rejecting intervals in which $\Delta_1 > K_1 \Delta_2$ and muscle artifact is lessened by rejecting intervals in which $B_2 > K_2 B_1$: where $\Delta_1 = 0.5-1.5$ Hz, $\Delta_2 = 1.5-3.5$ Hz, $B_1 = 19-25$ Hz and $B_2 = 25-50$ Hz.

The "regression removal" process, plus voltage threshold method, provides segments of relatively artifact-free EEG data, each preferably 600 milliseconds (ms.) long or longer. The computer system, in effect, stitches these intervals together to form a continuous artifact-free EEG segment, which is recorded in the computer memory. Each segment is preferably at least 2.5 seconds long (at least 4 intervals) and there are at least 48, and preferably 96, segments in the artifact-free EEG recording.

The 96 segments, each of 2.5 seconds, provide slightly over 4 minutes of EEG data. In a very cooperative patient, it may be possible to collect that 4 minutes of EEG data during a short 5-minute EEG recording session, but generally the EEG session will be 6 to 10 minutes long. That length of recording session is acceptable and without discomfort to most children and patients. Additional time is required for EP testing.

ANALYSIS OF DATA SPLIT-HALF SAMPLING

Sampling

The EEG "background activity" is assumed to be "stationary", i.e., any statistically adequate sample is equivalent to any other. Accordingly, the mass screening computer trades off time of data collection against number of channels. One channel, preferably, the vertex (CZ - REFERENCE) is always recorded as a "fiducial" channel to confirm stationarity of state. At least two additional channels are switched every 2.5 seconds in a random sequence which systematically constructs a Latin-square randomized sample of the other 18 electrodes in the 10/20 System, balancing for recency of recording. This statistically balanced EEG sample is used to derive the features defined below as if they had been recorded simultaneously from 19 channels in parallel, as with conventional EEG mapping instruments. The fiducial channel is challenged, using analysis of variance techniques (ANOVA) for heterogeneity of variance of the set of 2.5 second segments. Segments for which the analysis of the vertex fiducial load indicates significant departure from homogeneity of variance are discarded prior to the subsequent analyses.

ANALYSIS OF DATA

The sequence of segments is sorted, in the computer system, into two alternative split-half sets. For example, if there are 96 segments (each of 2.5 seconds) then one set ("even sample") contains 48 segments and the other set ("odd set") contains the 48 odd-numbered segments.

The EEG data in each of the segments in the two samples is analyzed to provide a group of features, or test scores, for each electrode (lead). Each test score (explained in detail below) is the value of a specific selected variable, for example, absolute power in 1.5-3.5 Hz band, which is compared to the distribution of data in a normal group, by Z-transformation (also explained in detail below). Each sample yields a set of test scores, each evaluated relative to the age-appropriate normative reference group.

Figure 2:
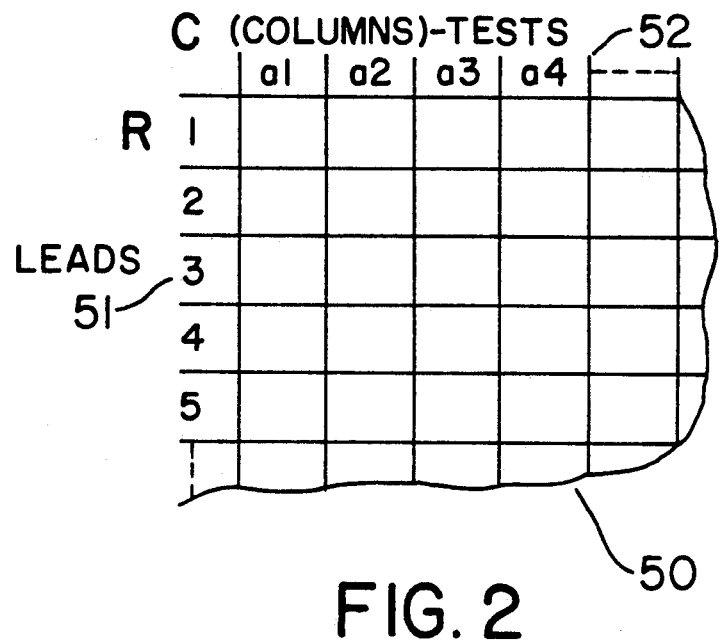
FIG. 2 is a matrix of test scores of a patient at each EEG electrode lead.
Figure 3:
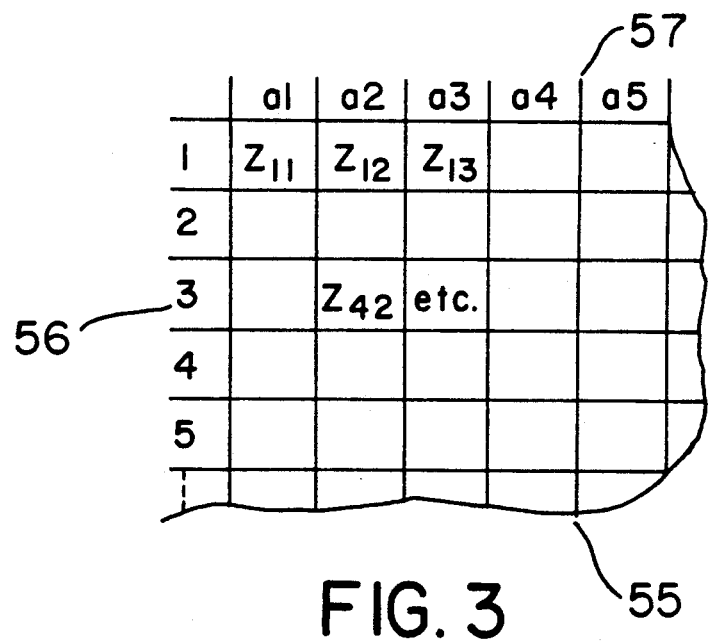
FIG. 3 is a matrix of test scores of a patient after transformation to measures which are proportional to probability.

The test scores of each set are arranged in a matrix 50 shown in FIG. 2 (the even sample is illustrated). The matrix is univariate because only a single feature is quantified for each test at each position in the matrix. In the matrix of FIG. 2 the R rows 51, labeled 1-19, are different electrode leads and the C columns 52 are the different quantitative features extracted from each lead. The test scores of the matrix 50 are subjected, in the computer system, to a correction, which is usually a logarithmic transform which corrects for nonGaussianity of the EEG feature distribution.

The variable, thus adjusted for Gaussianity, is then Z-transformed against the age-appropriate normative distribution, such that $$Z_i = [S_i - M_i] 6_i$$

where
$Z_i$ = Z score for variable i;
$S_i$ = value of variable i after log transform for Gaussianity;
$M_i$ = mean value of variable i in normative distribution after correction for age;

$\sigma_i$ = standard deviation of variable i in normative distribution.

This procedure yields the univariate matrix 55, which has R rows 56 and C columns 57, in the same format and content as matrix 50, but now transformed to measures proportional to probability. Additional columns can now be added to the univariate matrix which have composite variables representing aggregates of univariates corrected for their inter-correlations. Such multivariate features are called Mahalanobis distances, described below.

The computer system will then compare the corrected univariate plus multivariate Z-score matrix 55, for the even sample, with the corrected univariate plus multivariate Z-score odd sample. The odd sample has undergone the same transforms and corrections as the even sample. The same variables were extracted from both samples, that is, the same leads and tests found in corresponding locations in matrix 55 for the replicated even and odd samples.

If the test scores at any row R and column C are abnormal for both the even and odd samples at a predetermined $P_1$, for example, 0.01, then the abnormal finding is accepted as being valid. This is a replicated comparison of two independent scores for the same test. If no abnormal test scores replicate at the predetermined probability levels in both the even and odd samples, then the examination is considered to be within normal limits.

The chance of the two scores being significant by random error is proportional to the product of the predetermined probability level, P×P or $P^2$.

$$P_1 \times P_2 = \text{overall probability}$$
$$0.05 \times 0.05 = .0025$$

If P=0.01, then the probability of a replicated odd-even abnormal finding is 0.0001. That possibility of error is insignificant because it is much smaller than the number of test scores yielded by the quantitative analysis.

FEATURE EXTRACTION (TEST SCORES)

Preferably, the analysis of the data is in accordance with a predetermined set of power bands. Each channel is analyzed as 6 bands over the range 0.5 Hz to 50 Hz. The data from each channel is analyzed to yield the following features:

| | |
|---|---|
| 1. | Absolute power (microvolts squared - $\mu V^2$) in 0.5-1.5 Hz band (1) - low delta; |
| 2. | Absolute power ($\mu V^2$) in 1.5-3.5 Hz band ($\Delta 2$) - high delta; |
| 3. | Absolute power ($\mu V^2$) in 3.5-7.5 Hz band ($\theta$) - theta; |
| 4. | Absolute power ($\mu V^2$) in 7.5-12.5 Hz band ($\alpha$) - alpha; |
| 5. | Absolute power ($\mu V^2$) in 12.5-25 Hz band ($\beta 1$) - low beta; |
| 6. | Absolute power ($\mu V^2$) in 25-50 Hz band ($\beta 2$) - high beta; |
| 7. | "Total power" of each channel (1-25 Mz) in microvolts squared ($\mu V^2$). |
| 8. | Relative power (% of total power) in the $\Delta 1$ band; |
| 9. | Relative power (% of total power) in the $\Delta 2$ band; |
| 10. | Relative power (% of total power) in the $\theta$ band; |
| 11. | Relative power (% of total power) in the $\alpha$ band; |
| 12. | Relative power (% of total power) in the $\beta_1$ band; |
| 13. | Relative power (5 of total power) in the $\beta_2$ band; |
| 14-20. | Pearson product moment or polarity coincidence correlation coefficient between all the symmetric channels in order to provide an indication of waveshape synchrony or coherence. The coherence of power is also computed between pairs of symmetrical channels separately for all 6 frequency bands and the total EEG. |
| 21. | Total power ratio between each asymmetrical (homologous) pair of channels in order to provide an indication of power asymmetry. |
| 22-27. | Band power ratio in each frequency band $\Delta_1$, ($\Delta_2$, $\theta$, $\alpha$, $\beta_1$, $\beta_3$). |
| 28. | The total number of sharp waves detected in each channel. |

Each epoch (test period) will yield data in all 6 frequency bands. The epoch will be considered contaminated by artifact, and not used, if the absolute power in the low delta band or high beta band is greater than the absolute power in the high delta band or low beta band.

In order to satisfy the requirement for Gaussianity in order for requirement for parametric statistical analysis, the analysis of the data should conform to the following:

1. Total power in 1.5-25 Hz band should be evaluated.
2. Relative power (%) in $\Delta_2$, $\theta$, $\alpha$, $\beta_1$ should be computed (relative to total power, defined as in 1)
3. If relative power in each band is Xi, then $$\log \frac{(Xi)}{(100 - Xi)}$$

should be computed for each band in each channel to correct relative power for non-Gaussianity of measures 8-13.

4. For measures 1-7 and 14-27 above, log Xi should be computed to correct for non-Gaussianity.

Following the rules given above, the basic univariate abnormality matrix provides information about 359 tests, or Z-scores (see below).

Z-TRANSFORMS

Z-transformation is defined by the differences between the subject's values and mean values for the age-appropriate normative reference group, divided by the standard deviation (S.D.) of the reference group. The Z transformation characterizes the deviation of the subject's values from the reference group as a multiple of the S.D. Alternatively, other ways of comparing the subject's values to those of the reference group may be employed.

$$Z = \frac{x_i - \overline{X}}{\sigma x}$$

Z represents a neurometric measure equal to the difference between the subject's score $X_i$ and the age-appropriate reference group mean value X, divided by the S.D. of the reference sample; $\sigma_x$ is the standard deviation of the scores of normal individuals about the reference group mean.

The Z transformation provides a common metric of relative probability (units in which all scores are stated), regardless of their initial dimensionality (i.e., frequency, amplitude, synchronization, symmetry) for the univariate features (each test score). The univariate features (the test scores) are intercorrelated ("non-orthogonal"). The Mahalanobis distance, M, which corrects for the inter-correlation by taking the covariance matrix of the feature subset into account, is computed by the computer system. An acceptable metric for M is accomplished by Z-transformation of Multivariate Features, analogous to that described for univariate features. The multivariate Z-score, $Z_{mi}$, is defined as:

$$Z_M = (M_i - \overline{M_i})/6_i$$

where

M = patient multivariate feature i
M = population or self-norm mean of multivariate feature i
6 = standard deviation of reference norms for multivariate feature i

AGE REGRESSION EQUATIONS

The distribution of the relative power of the EEG for each frequency band and each anatomical region of the head depends to some extent on the age of the patient. If one had a sufficiently large number of normal patients, it might be possible to have the full set of measures extracted from a statistically adequate normal group for each age. However, as a practical matter, there is an alternative to testing about 70 normal groups, one for each year. First, a normal group for each age may be, in effect, synthesized by use of age regression and the resulting age regression equations stored in the computer memory.

Using these, the operator enters the patient's age on the keyboard 40 to correct for factors due to the age of the patient.

A number of polynomial functions must be used to describe the effect of age. A suitable table (Table I of U.S. Pat. No. 4,279,258, incorporated by reference herein, at column 11, line 34) provides the coefficients of the 4th order polynomials which describe effects of age for each frequency band. These polynomials are of the form:

$$\overline{Y}_i = a_0 + a_1 t + a_2 t^2 + a_3 t^3 + a_4 t^4$$

These 16 polynomials yield the relative power as a function of age in each frequency band, for each of 8 bipolar derivations (electrode). The value of standard deviation, corresponding to each measure (test) is a different constant for each derivation, and is also shown in the table. Similar tables for many hundreds of univariate and multivariate monopolar, bipolar and multipolar derivations have been published by the applicant (John et al, 1987).

SPIKE DETECTION

The "spikes" (sharp waves) in each channel are detected, counted and printed out on the display device. In general, sharp waves are defined as being 20–80 milliseconds in duration. They also exceed a selected amplitude, for example, 50 $\mu V$, a selected rate of rise, for example, 2 $\mu V/mS$, and exceed a selected sharpness (second derivative of EEG signal) defined as $d^2V/dT^2$, see U.S. Pat. No. 4,279,258 at column 6, lines 24–60. Significant deviations from a sliding, auto-aggressive moving average (AR MA) computed across a 20-second window are also computed. Sharp waves are defined as meeting both of these criteria. The computer detection of sharp waves is well-known in the EEG field. Preferably the software program to count the sharp waves is embodied in firmware in the computer system.

What is claimed is:

1. An electroencephalographic (EEG) system comprising:
    (a) a plurality of EEG electrodes, including a fiducial electrode, adapted to be removably secured to the scalp of the patient, each EEG electrode being a portion of a brain wave signal channel;
    (b) an amplifier means to amplify the analog microvolt level brain wave signals from the EEG electrodes in each brain wave channel, the amplifier means consisting of a plurality of fewer amplifiers than two-thirds the number of the EEG electrodes;
    (c) electronic switching means to sample the larger number of electrodes by the smaller number of amplifiers;
    (d) an analog/digital converter connected to the amplifiers to produce therefrom EEG data consisting of amplified and digitized brain wave signals;
    (e) a micro-processor based computer system means connected to the analog/digital converter to analyze the EEG data;
    (f) a patient stimulator means connected to and controlled by the computer system means to provide a selected pattern of stimulation to the patient to evoke the patient's brain wave responses in a set of evoked potential tests, each test being the brain wave evoked responses at a selected frequency range and at a selected electrode to a selected simulation;
    g) a computer memory means connected to the computer system means to store the test scores of normal groups to a set of evoked potential tests corresponding to the evoked potential tests given to the patient;
    (h) test score pair comparison means in the computer system means to form at least 24 pairs of test scores, each pair comprising two test scores from duplicated tests; to compare one test score of each pair with the other test score of the same pair, and to accept for further analysis only those pairs in which the two test scores of the pair are sufficiently alike within a predetermined definition;
    (i) normal comparison means in the computer system to compare accepted pairs of test scores with the normal group test scores of (g) and to identify, as being abnormal, those accepted pairs of test sources which are significantly deviant from the normal group test scores of (g);
    (j) signal means to signal the finding by (i) of abnormal test scores of the patient.

2. A system as in claim 1 wherein the test score pair comparison means of (h) arranges the test scores of each pair into respective odd and even matrices, each matrix consisting of rows and columns of test scores with the test scores of each pair being at corresponding locations in each matrix.

3. A system as in claim 1 wherein in (h) there are at least 48 pairs of the test scores.

4. A system as in claim 1 and including an EOG electrode adapted to be removably positioned proximate an eye of the patient to detect blinking, the EOG electrode being part of an EOG channel.

5. A system as in claim 4 and including means in the computer system of (e) to quantify the EEG data by spectral analysis using FFT (Fast Fourier Transform) and to detect artifact by regressing out the EOG channel from every EEG channel by comparison of the EOG channel and each EEG channel and to reject any intervals in which the voltage exceeds a multiple of the r m s voltage equal to 6×the standard deviation of means amplitude.

6. A system as in claim 1 and including mean feature means in the computer system of (e) to analyze the EEG data separately in the delta, theta, alpha and beta bands of brain wave frequencies and separately in each of the bands for each of the features of absolute power, relative power coherence and symmetry for each of the EEG channels and for homologous pairs of EEG channels to provide a set of mean feature values.

7. A system as in claim 6 and including correction means in the computer system of (e) to correct the mean feature values for Gaussianity.

8. A system as in claim 6 and including means to store age regression equations and to correct the mean feature values according to the age of the patient using the stored age-regression equations.

9. A system as in claim 1 including software means to join EEG data, meeting a predetermined definition of being artifact-free, into a continuous artifact-free record and to slice the joined artifact-free record into at least 48 segments each of at least 1 second in duration.

10. A system as in claim I wherein the computer system of (e) includes means to perform a spectral analysis of the EEG data using FFT (Fast Fourier Transform).

11. A system as in claim 1 wherein the computer system of (e) includes means to analyze the EEG data signals by average response computation.

12. A system as in claim 1 and further comprising a display means connected to the computer system to display the analog brain waves amplified by the amplifiers.

13. A system as in claim 1 wherein the significantly deviant level of (h) is defined to be at the $P<0.01$ level.

14. An electroencephalographic (EEG) system comprising:
   (a) a plurality of EEG electrodes adapted to be removably secured to the scalp of a patient, including a fiducial electrode, each EEG electrode being a portion of a brain wave signal channel;
   (b) an amplifier means to amplify the analog microvolt level brain wave signals form the EEG electrodes in each channel, the amplifier means consisting of a plurality of amplifiers which are fewer amplifiers than two-thirds the number of electrodes;
   (c) switching means to sample the larger number of EEG electrodes by the smaller number of amplifiers;
   (d) an analog/digital converter connected to the amplifiers to produce therefrom EEG data consisting of amplified and digitized brain wave signals;
   (e) a micro-processor based computer system connected to the analog/digital converter to analyze the EEG data;
   (f) a patient stimulator means connected to and controlled by the computer system to provide a selected pattern of stimulation to the patient to evoke the patient's brain wave responses in a set of evoked potential tests, each test being the brain wave evoked responses at a selected frequency range and at a selected electrode to a selected simulation;
   (g) a computer memory means connected to the computer system to store the test scores of normal groups to a set of evoked potential tests corresponding to the evoked potential tests given to the patient;
   (h) an EOG (electro-oculogram) electrode adapted to be removably attached to the patient's skin proximate the patient's eye and EOG amplification means to amplify the signals from the EOG electrode, the EOG amplification means connected to the analog/digital converter and the EOG electrode and EOG amplification means constituting an EOG channel;
   (i) quantification means in the computer system of (e) to quantify the EEG data by spectral analysis using FFT (Fast Fourier Transform) and to detect artifact by regressing out the EOG channel from every EEG channel by comparison of the EOG channel and each EEG channel; and to reject any of the intervals in which the voltage exceeds a multiple of the r m s voltage equal to $6\times$ the standard deviation of means amplitude;
   (j) test score pair comparison means in the computer system to form at least 24 pairs of test scores, each pair comprising two test scores from duplicated tests, to compare one test score of each pair with the other test score of the same pair to arrange the test scores of each pair into respective odd and even matrices each matrix consisting of rows and columns of test scores with the test scores of each pair being at the corresponding location in each matrix; and to accept for further analysis only those pairs in which the two test scores of the pair are sufficiently alike within a predetermined definition;
   (k) normal comparison means in the computer system to compare accepted pairs of test scores with the normal group test scores of (g) and to identify, as being abnormal, those accepted pairs of test scores which are significantly deviant from the normal group test scores of (g); and
   (l) signal means to signal the finding by (k) of abnormal test scores of the patient.

15. A system as in claim 14 and including mean feature means in the computer system of (e) to analyze the EEG data separately in the delta, theta, alpha and beta bands of brain wave frequencies and separately in each of the bands for each of the features of absolute power, relative power coherence and symmetry for each of the EEG channels and for homologous pairs of EEG channels to provide a set of mean feature values.

16. A system as in claim 15 and including correction means in the computer system of (e) to correct the mean feature values for Gaussianity.

17. A system as in claim 15 and including means to store age regression equations and to correct the mean feature values according to the age of the patient using the stored age-regression equations.

18. A system as in claim 14 including software means to join the EEG data, meeting a predetermined definition of being artifact-free into a continuous artifact-free record and to slice the artifact-free record into at least 48 segments each of at least 1 second in duration.

19. A system as in claim 14 wherein the computer system of (e) includes means to perform a spectral analysis of the EEG data using FFT (Fast Fourier Transform).

20. A system as in claim 14 wherein the computer system of (e) includes means to analyze the EEG data signals by average response computation.

21. A system as in claim 14 and further comprising a display means connected to the computer system to display the analog brain waves amplified by the amplifiers.

22. A system as in claim 14 wherein the significantly deviant level of (h) is defined to be at the P<0.01 level.

23. An eletroencephalographic (EEG) and electrocardiographic (EKG) system comprising:
(a) a plurality of EEG electrodes adapted to be removably secured to the scalp of the patient, including a fiducial electrode, each EEG electrode being a portion of a brain wave signal channel, and a plurality of EKG electrodes adapted to be removably secured to the skin of the patient to detect heart beats;
(b) a preamplifier means connected to the EEG electrodes to amplify the analog microvolt level brain wave signals from the EEG electrodes in each of the channels;
(c) a plurality of EKG amplifiers adapted at times to be removably connected to the plurality of EEG electrodes and adapted to be removably connected at other times to the EKG electrodes, the number of EKG amplifiers being less than two-thirds the number of EEG electrodes;
(d) switching means to sample the larger number of EEG electrodes by the smaller number of EKG amplifiers;
(e) an analog/digital converter means connected to the EKG amplifiers to produce EEG data consisting of amplified and digitized brain wave signals;
(f) a micro-processor based computer system means connected to the analog/digital converter to analyze the EEG data;
(g) a patient stimulator means connected to and controlled by the compute system means to provide a selected pattern of stimulation to the patient to evoke the patient's brain wave responses in a set of evoked potential tests, each test being the brain wave evoked responses at a selected frequency range and at a selected electrode to a selected simulation;
(h) a computer memory means connected to the computer system means to store the test scores of normal groups to a set of evoked potential tests corresponding to the tests given to the patient;
(i) means in the computer system means to compare the test scores of each patient with normal group mean test scores stored in the computer memory means; and
(j) display means to display the results of the test score comparisons and EKG heartbeat waveshapes.

24. A system as in claim 23 and further including a test score pair comparison means in the computer system means (e) to form at least 24 pairs of test scores, each pair comprising two test scores from duplicated tests, to compare one test score of each pair with the other test score of the same pair, and to accept for further analysis only those pairs in which the two test scores of the pair are sufficiently alike within a predetermined definition;
wherein the accepted pairs of test scores are compared in (i) with the normal group test scores of (h) to identify, as being abnormal, those accepted pairs of test sources which are significantly deviant from the normal group test scores of (h).

25. A system as in claim 24 wherein the test score comparison means arranges the test scores of each pair into respective odd and even matrices, each matrix consisting of rows and columns of test scores, with the test scores of each pair being at corresponding locations in each matrix.

26. A system as in claim 23 including an EOG (electro-oculogram) electrode adapted to be removably positioned proximate an eye of the patient to detect blinking.

27. A system as in claim 26 and including means in the computer system of (e) to quantify the EEG data by spectral analysis using FFT (Fast Fourier Transform) and to detect artifact by regressing out the EOG channel from every EEG channel by comparison of the EOG channel and each EEG channel; and to reject any intervals in which the voltage exceeds a multiple of the r m s voltage equal to 6×the standard deviation of means amplitude.

28. A system as in claim 23 and including mean feature means in the computer system of (e) to analyze the EEG data separately in the delta, theta, alpha and beta bands of brain wave frequencies and separately in each of the bands for each of the features of absolute power, relative power coherence and symmetry for each of the EEG channels and for homologous pairs of EEG channels to provide a set of mean feature values.

29. A system as in claim 28 and including correction means in the computer system of (e) to correct the mean feature values for Gaussianity.

30. A system as in claim 28 and including means to store age regression equations and to correct the mean feature values according to the age of the patient using the stored age-regression equations.

31. A system as in claim 23 including software means such that the EEG data meeting a predetermined definition of being artifact-free is joined into a continuous artifact-free record and then sliced into at least 48 segments each of at least 1 second in duration.

32. A system as in claim 23 wherein the computer system of (e) includes means to perform a spectral analysis of the EEG data using FFT (Fast Fourier Transform).

33. A system as in claim 23 wherein the computer system of (e) includes means to analyze the EEG data by average response computation.

34. A system as in claim 23 and further comprising a display means to display the analog brain waves amplified by the amplifiers.

35. A system as in claim 23 wherein the significantly deviant level of (h) is defined to be at the P<0.01 level.

36. An electroencephalographic (EEG) method comprising the steps of:
(a) removably attaching a plurality of EEG electrodes including a fiducial electrode to the scalp of the patient, each EEG electrode being a portion of a brain wave signal channel;
(b) connecting the EEG electrodes to an amplifier means to amplify the analog microvolt level brain wave signals from the EEG electrodes in each brain wave signal channel, the amplifier means consisting of a plurality of fewer amplifiers than two-thirds the number of the EEG electrodes;
(c) switching the amplifiers to the EEG electrodes to sample the larger number of electrodes by the smaller number of amplifiers;
(d) producing EEG data using an analog/digital converter connected to the amplifiers, the EEG data consisting of amplified and digitized brain wave signals;

(e) analyzing the EEG data in a micro-processor based computer system connected to the analog/digital converter;

(f) stimulating the patient in a preselected pattern of stimulations using a patient stimulator means connected to and controlled by the computer system means, the selected pattern of stimulation to the patient evoking the patient's brain wave responses to provide a set of evoked potential tests, each test being the brain wave evoked responses at a selected frequency range and at a selected electrode to a selected simulation;

(g) storing the test scores of normal groups to a set of evoked potential tests corresponding to the evoked potential tests given to the patient in a computer memory means connected to the computer system means;

(h) comparing pairs of test scores in the computer system from at least 24 pairs of different test scores, each pair comprising two test scores from duplicated tests by comparing one test score of each pair with the other test score of the same pair; and accepting for further analysis only those pairs in which the two test scores of the pair are sufficiently alike within a predetermined definition;

(i) comparing accepted pairs of test scores with the normal group test scores of (g) and identifying, as being abnormal, those accepted pairs of test sources which are significantly deviant from the normal group test scores of (g); and (j) signaling the finding by (i) of abnormal test scores of the patient.

37. A method as in claim 36 wherein the test score comparison means of (h) arranges the test scores of each pair into respective odd and even matrices, each matrix consisting of rows and columns of test scores with the test scores of each pair being at corresponding locations in each matrix.

38. A method as in claim 36 wherein in (h) there are at least 48 pairs of the test scores.

39. A method as in claim 36 and including the step of removably positioning an EOG electrode proximate an eye of the patient to detect blinking, the EOG electrode being part of an EOG channel.

40. A method as in claim 39 and quantifying the EEG data using means in the computer system of (e) to quantify the EEG data by spectral analysis using FFT (fast Fourier Transform) and detecting artifact by regressing out the EOG channel from every EEG channel by comparison of the EOG channel and each EEG channel and rejecting any intervals in which the voltage exceeds a multiple of the r m s voltage equal to 6×the standard deviation of means amplitude.

41. A method as in claim 36 and including using mean feature means in the computer system of (e) to analyze the EEG data separately in the delta, theta alpha and beta bands of brain wave frequencies and separately in each of the bands for each of the features of absolute power, relative power coherence and symmetry for each of the EEG channels and for homologous pairs of EEG channels to provide a set of mean feature values.

42. A method as in claim 41 and including using correction means in the computer system of (e) to correct the mean feature values for Gaussianity.

43. A method as in claim 41 and including storing age regression equations in computer system memory and correcting the mean feature values according to the age of the patient.

44. A method as in claim 36 including software means to join EEG data, meeting a predetermined definition of being artifact-free, into a continuous artifact-free record and to slice the joined artifact-free record into at least 48 segments each of at least 1 second in duration.

45. A method as in claim 36 and including the step of performing a spectral analysis of the EEG data using FFT (Fast Fourier Transform) using the computer system.

46. A method as in claim 36 and including the step of analyzing the EEG data signals by average response computation using the computer system.

47. A method as in claim 36 and including displaying the analog brain waves amplified by the amplifiers in display means connected to the computer system.

48. A method as in claim 36 wherein the significantly deviant level of (h) is defined to be at the $P<0.01$ level.

* * * * *